United States Patent [19]
Jackson et al.

[11] Patent Number: 4,596,570
[45] Date of Patent: Jun. 24, 1986

[54] NAPKIN WITH EXTENDABLE TABS

[75] Inventors: Wanda Jackson, Hightstown; Subramanian Srinivasan, East Brunswick, both of N.J.

[73] Assignee: Personal Products Company, Milltown, N.J.

[21] Appl. No.: 770,476

[22] Filed: Aug. 29, 1985

[51] Int. Cl.⁴ .............................................. A61F 13/16
[52] U.S. Cl. ................................................... 604/387
[58] Field of Search ............... 604/387, 386, 385, 389, 604/390, 397, 398, 400, 401

[56] References Cited
U.S. PATENT DOCUMENTS

| | | | |
|---|---|---|---|
| 2,512,713 | 6/1950 | Cahill | 604/387 |
| 2,838,048 | 6/1958 | Kowalski | 604/387 |
| 3,024,788 | 3/1962 | Lane | 604/387 |
| 3,454,008 | 7/1969 | Hendricks | 604/387 |
| 3,913,580 | 10/1975 | Ginocchio | 604/387 |

Primary Examiner—John D. Yasko
Attorney, Agent, or Firm—Jason Lipow

[57] ABSTRACT

A sanitary napkin is provided which is capable of being used as is or can be elongated by simple action by the user. The napkin comprises short tabs having pleats therein which can be unfolded to render the napkin longer.

9 Claims, 9 Drawing Figures

U.S. Patent  Jun. 24, 1986  Sheet 1 of 3  4,596,570

NAPKIN WITH EXTENDABLE TABS

BACKGROUND OF THE INVENTION

This invention relates to sanitary napkins in general and, in particular, to napkins to be worn by adhering to the crotch portion of an undergarment.

The art is now replete with various suggestions for adhesively attached sanitary napkins. Such products generally consist of an elongated absorbent element optionally enclosed in a body fluid pervious cover on the body facing side thereof and a body fluid impervious cover on the garment facing side thereof. The cover materials are commonly extended beyond the tranverse ends of the absorbent element and sealed together to form short, sealed tabs to fully enclose the absorbent element.

A pressure-sensitive adhesive element is provided on the garment facing side of the napkin, commonly in the form of a longitudinal strip or strips of adhesive extending from near one transverse end of the absorbent element to near the other transverse end and is centrally located with respect to the longitudinal ends.

While, in the main, such products have performed adequately and have also proven to be comfortable to most wearers, for some women and at certain times, there has been evidenced a willingness to sacrifice comfort, to some degree, in favor of greater protection. Specifically, at certain times, it is desirable to have a longer napkin. For example, for nighttime use changes are less frequent and hence protection is paramount while body movements are less frequent and hence comfort is not impaired by such a longer napkin. Also, since flow rates of menstrual fluid vary greatly for some women during her monthly cycle, there are times when extra protection is imperative and times when far less protection is needed. Generally, because of the expense and bother of purchasing assorted sized napkins, women have compromised and chosen only one size, albeit less than ideal at any given time.

Accordingly, there is a need for a napkin which can provide both the comfort of a short napkin with the length of a long napkin when such extra protection is desired.

SUMMARY OF THE INVENTION

In accordance with the teachings of this invention, a napkin is provided which can be converted by simple action on the part of the wearer, from a relatively short napkin to a relatively long napkin, and which in either mode, provids the user with the desired protection and comfort.

Specifically, a napkin is provided with a central elongated absorbent element having a body facing side, a garment facing side, longitudinally extending edges and transverse ends.

The body facing side is covered by a menstrual fluid pervious cover and the garment facing side is covered by a fluid impervious cover. The two covers extend longitudinally beyond the transverse ends of the central core to form elongated tabs and one or more elongated pressure-sensitive adhesive elements are provided on the external most garment facing side of the napkin which elements extend longitudinally to substantially the tranverse ends of the tabs.

The tabs are provided with a plurality of transverse fold lines, dividing the tabs into panels with the fold lines biasing the panels to fold upon themselves in the pattern of body facing side to body facing side folds alternating with garment facing side folds so as to form a series of pleats in said tabs, with the body facing side of the pleated tabs exposing essentially only the body fluid pervious cover and the garment side of the pleated tabs exposing essentially only body fluid impervious cover The pleats are conveniently held together by the pressure-sensitive adhesive.

In use, the user may employ the sanitary napkin with the tabs fully pleated and hence in its shortest form or may convert the napkin by unfolding one or more of the pleats to lengthen the tabs.

Preferably, to increase the protective nature of the tabs, interposed between the pervious body facing cover and the impervious garment facing cover, at least in the area of the tabs, is a relatively thin, absorbent layer. For ease of manufacture, this layer may extend throughout the entire length of the product from tab end to tab end and either overlie the garment facing side of the central absorbent element or even overlie the body facing side of said element.

In one embodiment, the adhesive element extends continuously and longitudinally with the napkin from near the transverse end of a first tab to near the transverse end of the other tab. In this embodiment, the adhesive must be chosen and applied in such quantity that the adhesive will release from itself to allow the user to unfold the pleats.

In another embodiment, the longitudinally extending adhesive is applied discontinuously in the area of the pleats so that adhesive is applied only on alternating panels. In this case, the adhesive is chosen so as to release from the adjacent panel.

The precise configuration of the pleats may vary in several ways and still allow full enjoyment of the advantages of this invention. For example, the pleats may be folded so that all the pleats overlie each other. Alternatively, the pleats may be folded so that only part of one pleat overlies the next adjacent pleat thus forming a staggered profile for the tab. The pleats may be folded so that all extend beyond the transverse end of the absorbent element, or may be folded to overlie the garment side of the absorbent layer. Other workable variations will occur to one skilled in the art as a result of the disclosure herein.

BRIEF DESCRIPTION OF THE DRAWINGS

FIG. 3a is a transverse cross-sectional view of the napkin of FIG. 1, taken through line 3a—3a;

DETAILED DESCRIPTION OF THE INVENTION

Figure 1:
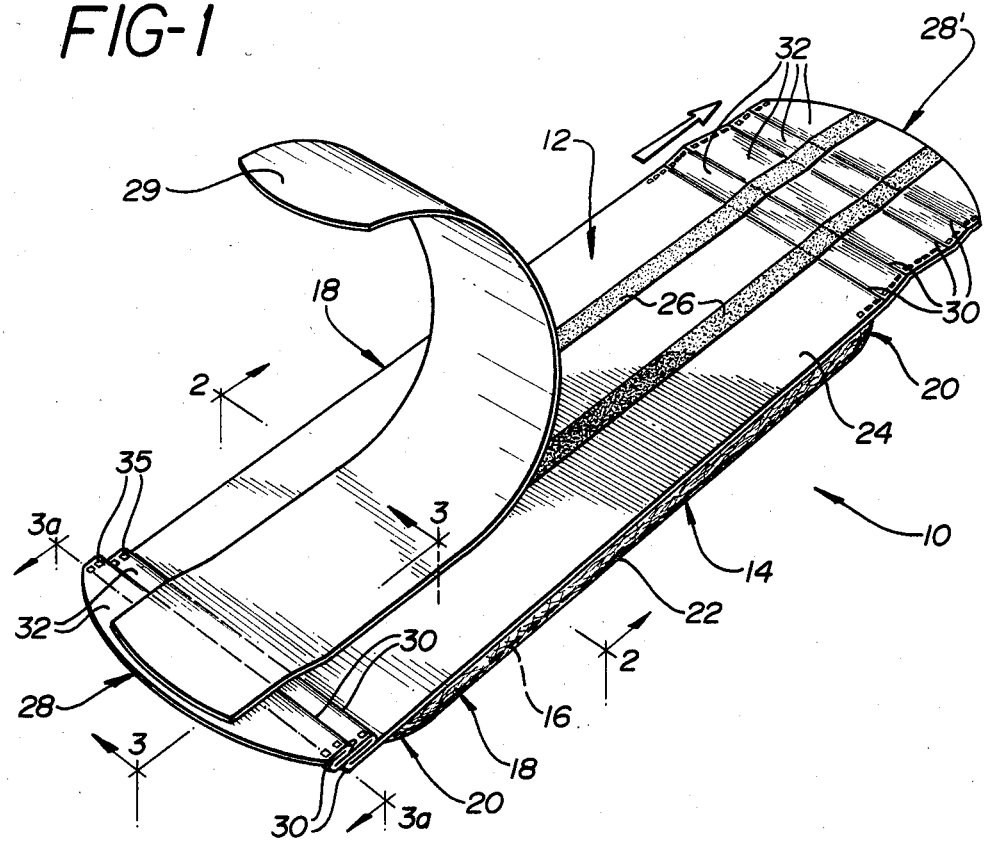
FIG. 1 is a perspective view of a sanitary napkin incorporating the teachings of this invention as viewed toward the garment facing side thereof.

Referring now to FIGS. 1-3 and 3a, illustrated therein is a specific embodiment of the invention, napkin 10. As viewed in FIG. 1, the garment facing side 12 is uppermost and the body facing side 14 is essentially hidden.

The napkin 10 consists of an elongated absorbent element 16 having a body facing side, a garment facing side, longitudinally extending edges 18 and transverse ends 20. The choice of materials for use in the pad of this invention is not critical and may be any of the well known absorbent materials utilized in products of this nature.

Preferably, the pad comprises loosely associated absorbent hydrophilic material such as cellulose fibers, e.g., wood pulp, regenerated celulose or cotton fibers. Such fibers may be chemically or physically modified and the pad may include such fibers in combination with other materials, both natural and synthetic, such as hydrophilic foams, hydrophilic polymers or the like. A material of choice is wood pulp which is inexpensive, readily available and lends itself well to the teachings of this invention.

Overlying the body facing surface 14 of the napkin 10, i.e., the side of the napkin to be worn against the body of the user, is a body fluid pervious cover 22. The cover 22 may be any woven or nonwoven material pervious to body fluid striking its surface, such covers being well known in the art. In a preferred embodiment, the cover comprises thermoplastic material capable of being fusibly sealed to another element of the napkin, e.g., by heat, pressure, sonic sealing, or the like.

A material of choice for the cover is a fabric comprising heat bondable polyester/polyethylene conjugate fibers. Such conjugate fibers are fibers which comprise a polyester core surrounded by a sheath of polyethylene. Preferably, the conjugate fibers employ high density polyethylene, that is, linear polyethylene that has a density of at least 0.94 gm/cc and a Melt Index (as determined by ASTMD-1288E method, employing the parameters of 190° C. and 2160 gms.) of greater than 1, preferably greater than about 10, and more preferably from about 20 to about 50. The fibers may comprise from about 40 to about 60 percent, by weight polyester and, preferably, from 45 to 55 percent by weight polyester, with the remainder being polyethylene. Such fibers may be used in deniers of from 1 to about 6 and may be from about ½ inch (1.27 cm.) to about 3 to 4 inches (7.62 to 10.16 cm.) long. The fabric comprising such fibers is stabilized by applying heat thereto under essentially zero pressure whereby thermal bonding takes place without destroying the integrity of the fibers.

Overlying the garment facing surface 12 of the napkin 10 (the side worn away from the body of the user) is a body fluid impervious cover 24. The cover 24 is provided to preclude body fluid from passing onto an udergarment and may be constructed of any material suitable for this purpose. For example, the cover 24 may be a polymeric film such as polyethylene, polypropylene, or cellophane or may be normally fluid pervious material that has been treated to be impervious such as a fluid repellant paper. Advantageously, the cover 24 is a heat bondable material such as polyethylene which can be bonded to cover 22 to completely enclose pad 16.

In an embodiment not shown, an outer cover, which comprises a nonwoven fabric, overlies the cover 24 on the garment side of the napkin 10. This fabric outer layer is provided for aesthetic purposes and for its soft feed. This outer cover may, in fact, be no more than extensions of the cover 22.

Figure 2:
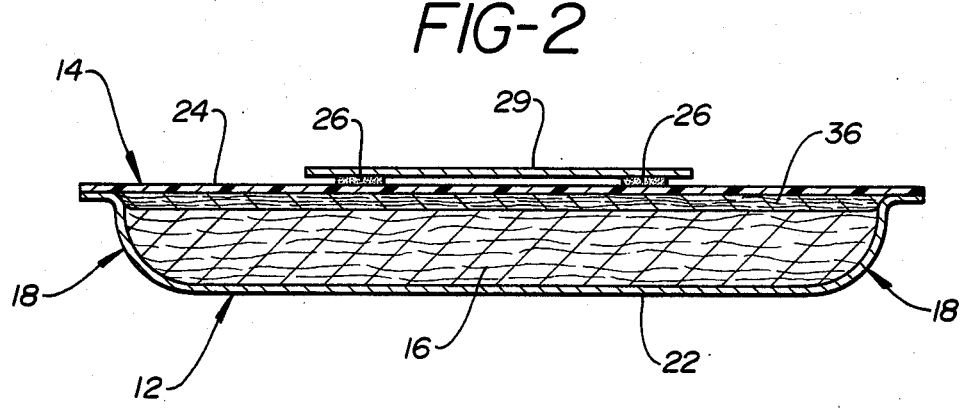
FIG. 2 is a transverse cross-sectional view of the napkin of FIG. 1, taken through line 2—2.

As best viewed in FIGS. 1 and 2, the garment facing side of the napkin 10 is provided with pressure-sensitive adhesive elements 26 for adhering the napkin to the crotch portion of the wearer's undergarment. As shown in this specific embodiment these adhesive elements 22 are in the form of two longitudinally extending bands although it will be understood by those skilled in the art that many variations in the number and shape of these adhesive elements are possible. The pressure-sensitive adhesive may be any of the already known compositions suitable for this purpose including, for example, the water based pressure-sensitive adhesives such as the acrylate adhesives, e.g., vinyl acetate-2 ethyl hexyl acrylate copolymer which are generally combined with tackifiers such as, for example, ethylene amine. Alternatively, the adhesive may comprise the rapid setting thermoplastic (hot melt) adhesives such as block copolymers exemplified by styrene and butadiene/styrene copolymers. The adhesive elements may also comprise a two-sided adhesive tape.

The tenacity and releasability of such pressure-sensitive adhesive elements may be varied to suit the purpose of this invention by techniques well known to the art of adhesive formulating.

The adhesive areas are protected by a release strip 29 to avoid undesired adhesion prior to use. The release strip 29 may be made of any suitable sheet-like material which adheres with sufficient tenacity to the adhesive elements 26 to remain in place, but which can be readily removed when the napkin 10 is to be used. A particularly useful material is a semi-bleached kraft paper, the adhesive contacting side of which has been silicone coated to provide for easy removal from the adhesive just prior to use.

Figure 3:
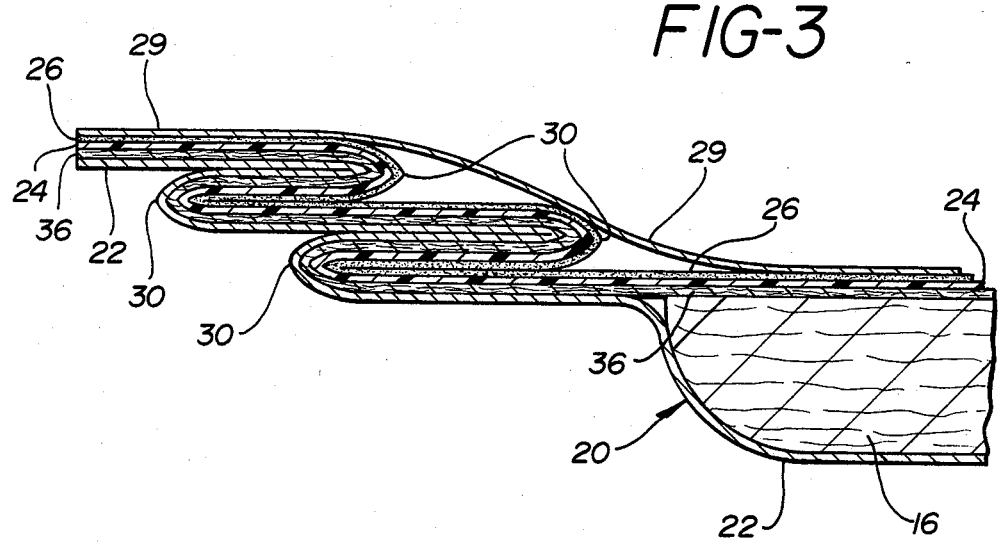
FIG. 3 is a fragmentary cross-sectional view of the napkin of FIG. 1, taken through line 3—3.
Figure 3A:
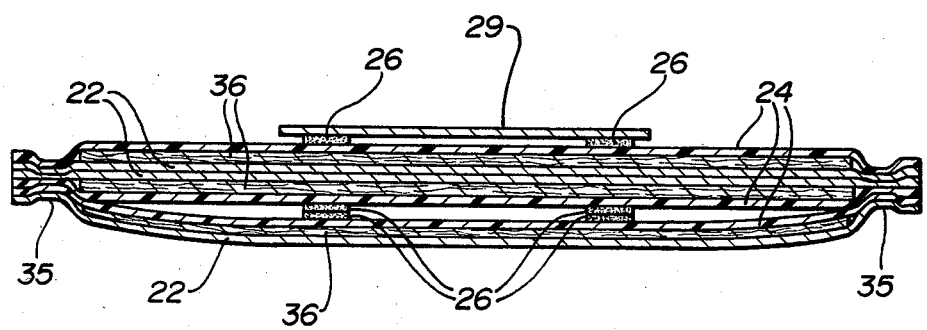

In accordance with the teachings of this invention, and as best viewed in FIGS. 1 and 3, the pervious cover 22 and the impervious cover 24 extend longitudinally beyond the transverse edges 20 of the absorbent element 16, and are joined to form elongated tabs 28 and 28' which extend beyond the transverse edges 20. As illustrated in FIG. 1, tab 28' is in the fully extended position whereas tab 28 is in the pleated position.

Referring to tab 28' it can be seen that the tab is provided with a plurality of transverse fold lines 30 which fold lines 30 divide the tabs into panels 32. The fold lines are biased so that a panel may be folded upon an adjacent panel in face to face relationship in the pattern of body facing side to body facing side relationship alternating with garment facing side to garment facing side relationship. Thus a series of pleats are formed in the tabs when the panels are so folded about the fold lines.

As is best illustrated in FIG. 1 when the panels are folded into pleats, the resulting tab (tab 28 in FIG. 1) is relatively short. With both tabs in this condition, the napkin is similar in dimensions to the typical adhesively attached napkins now on the market and may be used in this fashion. To insure that the pleats remain in place, preferably the longitudinally edges are provided with releasable means for adhering the adjacent panels together to supplement the adhesive elements 26. As best viewed in FIGS. 1 and 3a, such means may be seals 35 which may be accomplished, for example, by heat sealing, adhesive sealing or crimping.

Again, as best viewed in FIG. 1, when it is desired to utilize a longer napkin, the end of a pleated tab may be gripped and urged in the direction shown by the arrow adjacent tab 28' in FIG. 1, whereby one or more of the pleats will unfold and provide the desired added length. Tab 28' of FIG. 1 illustrates such an elongated tab fully unfolded.

In its fully pleated configuration the napkin may have an overall length of from 5 to 9 inches with the fully pleated tabs extending about 0.5 to 2 inches from each transverse end of the central absorbent 16. Sufficient pleating should be provided so that in its unpleated condition the napkin has an overall length of from 6 to 12 inches with the tabs extending about 1 to 5 inches from each transverse end of the absorbent element 16. For example, a suitable product is provided with an absorbent element having a length of 6 inches and tabs, which when unpleated are each 2 inches long. The tabs are divided in 4 panels each measuring 0.5 inches in the longitudinal direction and foldable into 2 pleats whereby, in its fully pleated condition, the tabs extend 2 inches from the transverse end of the absorbent element 16.

It will be understood that while tabs consisting of only superimposed and joined extensions of body fluid pervious cover 22 and body fluid impervious cover 24 will provide a reasonable measure of protection, preferably the tabs have, sandwiched between these covers, a relatively thin layer 35 of absorbent material. The layer 35 should be quite thin relative to the thickness of absorbent element 16, e.g., less than 50% of the thickness of absorbent element 16, and may be comprised of any of the well known absorbent materials such as those described in connection with absorbent element 16. Preferably the material of choice for layer 36 is one which is even more retentive of body fluids than element 16 and also has rapid wicking properties. Retention may be accomplished by utilizing in layer 35 one or more of the so called superabsorbent materials now known and which have the properties of high liquid retention, e.g., the crosslinked acrylate polymers. Wicking may be enhanced by using wetting agents or by densification of this layer 35 to increase capillary forces. A useful material for layer 35 is, for example, a web comprising 75% by weight of comminuted wood pulp and 25% by weight of powdered crosslinked polyacrylate having a density of 0.35 grams per cubic centimeter and a thickness of 1.0 millimeters.

In the embodiment illustrated in FIGS. 1-3 and 3a, the layer 35 is dimensioned so as to not only be present between the cover layers in the tab portions of the product but instead is as wide as the absorbent element 16 and as long as the unpleated napkin. Thus layer 35 is coextensive with impervious cover 24 and overlies the garment facing side of absorbent element 16. It will be understood that, alternatively, layer 35 may be provided on the other side of absorbent element 16, i.e., on the body facing side between cover 22 and element 16, and will function satisfactorily.

Figure 4:
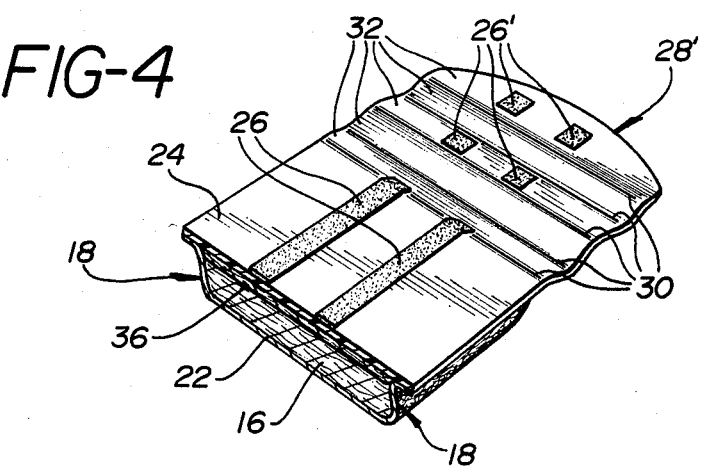
FIG. 4 is a fragmentary perspective view of one end of a napkin incorporating an alternative embodiment of this invention.

Referring now to FIG. 4, illustrated there is a fragmentary view of an alternative embodiment to the napkin shown in FIGS. 1-3 (wherein reference numbers relating to like parts have been maintained). Shown in FIG. 4 is tab 28' with adhesive element 26 being discontinuous in the area of the panels 32 so that adhesive spots 26' are applied on alternate adjacent panels 32. In this manner less adhesive is used and the adhesive may be designed to release from the cover 26 material instead of releasing from itself, as in the prior embodiment.

Figure 5:
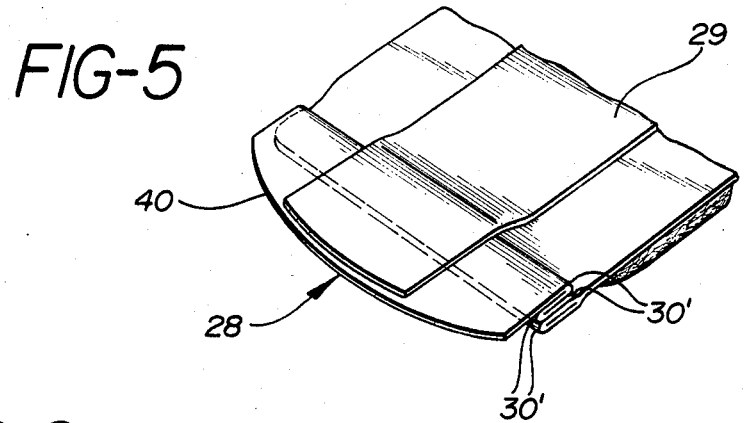
FIG. 5 is a fragmentary perspective view of one end of a napkin incorporating another alternative embodiment of this invention.
Figure 6:
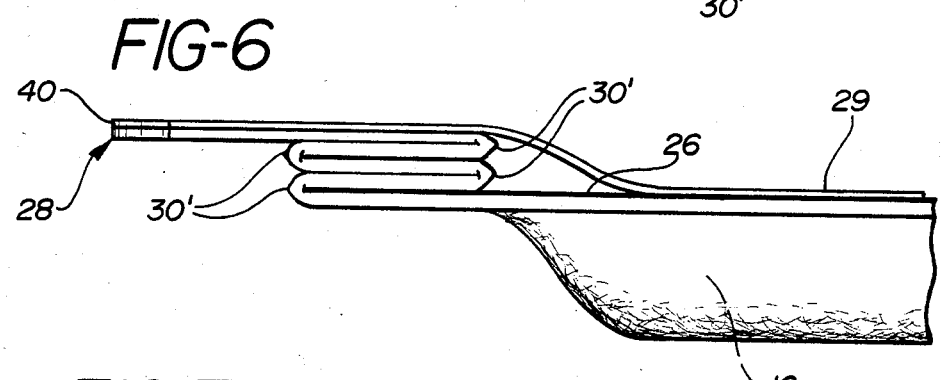
FIG. 6 is a fragmentary side elevational view of the end of the napkin illustrated in FIG. 5.

The embodiment illustrated in FIGS. 1 and 3 employs fold lines 30 so spaced as to result in pleats which partially overlie each other so as to provide a staggered pleated arrangement. Various other configurations are possible and may in some instances be preferred. One such alternative arrangement is illustrated in FIGS. 5 and 6 wherein the fold lines 30' are provided so spaced as to result in each of the pleats fully overlying each other.

Figure 7:
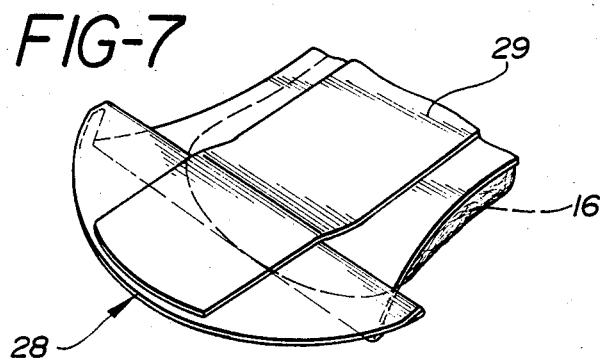
FIG. 7 is a fragmentary perspective view of one end of a napkin incorporating still another alternative embodiment of this invention.
Figure 8:
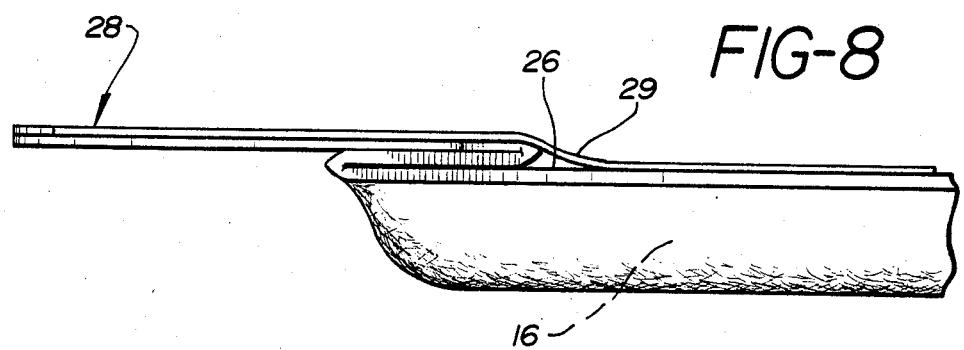
FIG. 8 is a fragmentary side elevational view of the end of the napkin illustrated in FIG. 7.

Such a configuration insures that the extreme end portion 40 of the tab 28 is completely smooth and free of pleats. In another variation shown in FIGS. 7 and 8, the pleats, by virtue of the placement of the fold lines, totally lie over the extreme end of the absorbent element 16, leaving the remainder of the tab smooth and free of pleats. Undoubtedly, alternative configurations will occur to those skilled in the art based on the teachings herein.

What is claimed is:

1. A sanitary napkin comprising a central absorbent element having a body facing side, a garment facing side, longitudinally extending edges and transverse ends;
   a body fluid pervious cover on the body facing side;
   a body fluid impervious cover on the garment facing side;
   said covers extending longitudinally beyond said central core to form elongated tabs;
   at least one longitudinally extending adhesive element on the garment facing side of said tabs;
   said tabs having a plurality of transverse folds dividing said tabs into transverse panels;
   said folds biasing said panels to fold upon adjacent panels in face to face relationship in a pattern of body facing side to body facing side relationship alternating with garment facing side to garment facing side relationship to form a plurality of pleats in said tabs;
   said pleats being held releasably in place by said adhesive elements.

2. The napkin of claim 1 wherein said tabs further comprise an absorbent layer between said extended covers.

3. The napkin of claim 2 wherein said absorbent layer extends, longitudinally, from the end of a first of said tabs, overlies a side of the absorbent element and extends to the end of the second of said tabs.

4. The napkin of claim 3 wherein said absorbent layer overlies the garment facing side of said absorbent element.

5. The napkin of claim 3 wherein said absorbent layer overlies the body facing side of said absorbent element.

6. The napkin of claim 1 wherein said longitudinally extending adhesive element is discontinuous so that adhesive is provided on alternate adjacent panels.

7. The napkin of claim 1 wherein said folds are positioned to produce pleats partially overlying each other in staggered relationship.

8. The napkin of claim 1 wherein said folds are positioned to produce pleats fully overlying each other.

9. The napkin of claim 1 wherein said folds are positioned to produce pleats which totally lie over the absorbent element.

* * * * *